United States Patent [19]

Dörschug et al.

[11] Patent Number: 5,270,176
[45] Date of Patent: Dec. 14, 1993

[54] METHOD FOR THE SELECTIVE CLEAVAGE OF FUSION PROTEINS WITH LYSOSTAPHIN

[75] Inventors: Michael Dörschug, Bochum; Gerhard Seipke, Wiesbaden, both of Fed. Rep. of Germany

[73] Assignee: Hoechst Aktiengesellschaft, Frankfurt am Main, Fed. Rep. of Germany

[21] Appl. No.: 905,482

[22] Filed: Jun. 29, 1992

Related U.S. Application Data

[63] Continuation of Ser. No. 715,894, Jun. 19, 1991, abandoned, which is a continuation of Ser. No. 272,853, Nov. 12, 1988, abandoned.

[30] Foreign Application Priority Data

Nov. 20, 1987 [DE]  Fed. Rep. of Germany ....... 3739347

[51] Int. Cl.$^5$ .................... C07K 3/08; C12N 15/62
[52] U.S. Cl. .................. 435/69.7; 435/257.3; 530/412
[58] Field of Search ............ 435/69.7, 172.3; 530/412; 935/47

[56] References Cited

U.S. PATENT DOCUMENTS

| | | | |
|---|---|---|---|
| 4,743,679 | 5/1988 | Cohen et al. | 935/47 |
| 4,751,180 | 6/1988 | Cousens et al. | 435/68 |

FOREIGN PATENT DOCUMENTS

| | | |
|---|---|---|
| 0035384 | 2/1981 | European Pat. Off. |
| 0207402 | 6/1988 | European Pat. Off. |

OTHER PUBLICATIONS

Marston et al. *Biochem. J.*, (1986) 240, pp. 1–12.
Iversen et al. *Eur. J. Biochem.*, (1973) 38, pp. 293–300.
K.-K. Han et al., *Int. J. Biochem.* vol. 15, No. 7, pp. 875–884 (1983).
G. Sloan et al., *Int. J. of Systematic Bacteriology*, vol. 32, No. 2, pp. 170–174 (1982).
G. Sloan et al., *Biochem. J.*, vol. 167, pp. 293–296 (1977).

*Primary Examiner*—Robert J. Hill, Jr.
*Assistant Examiner*—John D. Ulm
*Attorney, Agent, or Firm*—Finnegan, Henderson, Farabow, Garrett & Dunner

[57] ABSTRACT

The invention relates to a method for the preparation of polypeptides or proteins by enzymatic cleavage of the oligo- or polyglycine sequence of a fusion protein using an endoprotease.

5 Claims, No Drawings

METHOD FOR THE SELECTIVE CLEAVAGE OF FUSION PROTEINS WITH LYSOSTAPHIN

This application is a continuation of application Ser. No. 07/715,894, filed Jun. 19, 1991, now abandoned, which is a continuation of Ser. No. 07/272,853, now abandoned.

The invention relates to a method for the preparation of polypeptides or proteins by enzymatic cleavage of a fusion protein.

The increasing importance of recombinant DNA technology for obtaining polypeptides and proteins requires the development of new methods for enriching and purifying the products, which are appropriate for the altered starting materials.

At present, a large number of proteins is synthesized in the microorganism as fusion protein, i.e. the sequence of a foreign protein is placed in front of the amino acid sequence of the desired polypeptide (F.A.O. Marston, Biochem. J. 240 (1986) 1-12). In general, the fusion proteins precipitate in the cell, because they are sparingly soluble or insoluble, as what are called inclusion bodies and are thus protected from proteolytic degradation. This ensures high yields and ease of isolation of this primary gene product.

However, in order to obtain the desired polypeptide it has to be separated out of the fusion protein by enzymatic or chemical cleavage. Chemical methods are often used for cleavage, because it is most straightforward to make them appropriate for the sparingly soluble nature of the fusion protein. Incomplete cleavage or formation of byproducts by irreversible derivatization of amino acid side-chains are, however, observed with virtually all chemical methods. There is also always a danger of non-specific degradation of polypeptide chains (K.-K. Han et al., Int. J. Biochem. 15, (1983) 875-884). Moreover, the use of chemical methods is restricted because the specificity of the cleavage is determined predominantly by a single amino acid which, in the nature of things, is often also present in the desired polypeptide.

Enzymatic fragmentations can be carried out under considerably milder conditions. However, general difficulties arise here due to the fact that the sparingly soluble fusion protein must be dissolved and maintained in solution using detergents, urea or guanidine hydrochloride, that is to say conditions under which enzymes are often inactivated. It is often impossible to use proteases which recognize only a single specific amino acid because this amino acid is also present in the desired protein. On the other hand, the availability of proteases which recognize and cleave only very specific, rare sequences of several amino acids is low. Thus, it is necessary to find a method of cleavage specific for each product. Hence, it is additionally desirable to have a universally applicable cleavage method which cleaves only at very particular, rare amino acid sequences without damaging the protein and which can also be applied to sparingly soluble fusion proteins.

Lysostaphin is disclosed in the literature as an enzyme which degrades cell walls and is secreted by Staphylococcus simulans (NRRL B-2628; Sloan et al., Int. J. of Systematic Bacteriology, Vol. 32, No. 2 (1982) 170-174) into the medium. This enzyme lyses virtually all known Staphylococcus species but no other bacterial species. It has hitherto been assumed that lysostaphin endoprotease only cleaves, very selectively, the polyglycine bridges in the murein sacculus of the Staphylococci (Iversen and Grov, Eur. J. Biochem. 38 (1973) 293-300). Additionally disclosed have been transpeptidization experiments with lysostaphin catalysis using short synthetic glycylpeptides (G. L. Sloan et al., Biochem. J. 167 (1977) 293-296). We have now found, surprisingly, that lysostaphin endoprotease also cleaves fusion proteins having an oligo- or polyglycine sequence. It is apparently unnecessary for the selectivity of the cleavage that this sequence be bound into the specific steric relationships of a bacterial cell wall.

This makes it possible to eliminate specifically the desired protein from a fusion protein under mild conditions.

The present invention relates to a method for the preparation of polypeptides or proteins by enzymatic cleavage, which comprises cleavage of a fusion protein having the sequence

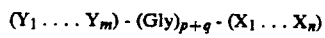

$$(Y_1 \ldots Y_m) - (Gly)_{p+q} - (X_1 \ldots X_n)$$

where $(Y_1 \ldots Y_m)$-$(Gly)_p$ represents the sequence which is to be eliminated and $(Gly)_q$-$(X_1 \ldots X_n)$ represents the polypeptide or protein, X and Y denote, independently of one another, natural amino acids, m and n denote numbers greater than 1, p and q each denotes a number greater than 0 and p+q together denote a natural number between 2 and 100, and if $Y_m$ represents Gly it is possible for p+q also to be <2 and p to be 0, and if $X_1$ represents Gly it is possible for p+q also to be <2 and q to be 0, with an endoprotease specific for oligo- or polyglycine sequences, and subjecting the polypeptide or protein which is liberated by this to further chemical or enzymatic treatment where appropriate, or directly processing it further.

Dependent on the value of the indices p and/or q, the sequence which is to be eliminated and/or the polypeptide or protein is optionally subjected to further enzymatic cleavages.

$(Y_1 \ldots Y_m)$ is a natural or artificial protein sequence as customarily employed for the preparation of fusion proteins. Suitable examples are β-galactosidase, enzymes of tryptophan metabolism or parts of these protein molecules which, in general, result in insoluble products, as well as polypeptide sequences which facilitate rapid enrichment of a soluble fermentation product (for example antibodies).

$(X_1 \ldots X_n)$ represents a pharmacologically active polypeptide or protein or represents a higher molecular weight precursor from which the desired biologically active form is obtained by further processing such as folding, with the production of correct disulfide bridges, and/or specific cleavage of the polypeptide chains. One example of this would be preproinsulin, from which insulin is produced.

The residues X and Y represent, independently of one another, naturally occurring amino acids (see, for example, Schrödder, Lübke "The Peptides" Vol. I, New York 1965, Pages 137-270 and Houben-Weyl "Methoden der organischen Chemie" (Methods of Organic Chemistry) Vol. 15/1 and 2 (Synthesis of Peptides), Georg Thieme Verlag Stuttgart 1974, Annex). The following may be particularly mentioned: Gly, Ala, Ser, Thr, Val, Leu, Ile, Asp, Asn, Glu, Gln, Cys, Met, Arg, Lys, Hyl, Orn, Cit, Tyr, Phe, Trp, His, Pro and Hyp.

An endoprotease specific for oligo- and polyglycine sequences is to be understood to be, in particular, lysostaphin (manufacturer: (®)SIGMA Chemie GmbH, Deisenhofen; cf. also Recsei et al., Proc. Natl. Acad. Sci. USA, Vol. 84, (1987) 1127-1131).

The desired product $(X_1 \ldots X_n)$ is connected to a protein $(Y_1 \ldots Y_m)$ by any desired glycine sequence $(Gly)_{p+q}$. Preferred fusion proteins are those in which p+q together denotes a natural number between 2 and 100. A larger number of consecutive glycine residues may in this connection have a beneficial effect on the reaction rate, because the cleavage site is more accessible. However, the same effect is also achieved when short oligoglycine sequences are flanked by one or more other amino acids which do not sterically hinder the enzyme during cleavage. Accordingly, the length of the connecting piece should be made appropriate for the structural properties of the fusion partners.

The cleavage conditions can be varied within a very wide range and thus made appropriate for the properties of the fusion protein. Thus, it is possible for the enzyme/substrate ratio to be, for example, between 1:1 and 1:1,000,000, and for the reaction to be carried out in a pH range from 6 to 9, preferably in the range 7 to 8, preferably at a temperature of 20°-60° C., especially of 32°-42° C. It is also possible, where appropriate, depending on the degree of the sparing solubility of the fusion protein, to add an auxiliary, for example urea, detergents or guanidine hydrochloride, which keeps the fusion protein in solution. Although the cleavage takes place most rapidly when virtually complete solution of the fusion protein is possible without addition of denaturing agents, the lysostaphin endoprotease is not inactivated by the presence of urea, merely the enzymatic reaction is slowed down. This fact can be utilized for the cleavage of particularly sparingly soluble fusion proteins. On the other hand, it is also possible in principle to carry out successfully, with a corresponding increase in the reaction time, fragmentations of merely suspended inclusion bodies. In the case of solutions of the fusion protein—with or without denaturing agent—it is also possible to use advantageously the lysostaphin endoprotease in carrier-bound form (immobilized enzyme) and recover it for reuse. Examples of suitable enzyme carriers are inorganic carriers such as aluminum silicates as well as polymeric organic carriers such as agaroses, for example (®)Affi-Gel 10 (from Bio Rad), celluloses, modified polyacrylamide gels which have amino or hydroxyl groups, or ease organic copolymers of acrylamide, methacrylates or methacrylamide and maleic anhydride. The preparation of appropriate carrier-bound enzymes is described, for example, in Halwachs et al., Biotechnology and Bioengineering XIX (1977) 1667-1677 (immobilization on aluminum silicate) or German Offenlegungsschrift 2,927,534 (immobilization on cellulose).

The method according to the invention is not only suitable for the selective cleavage of fusion proteins but also applicable generally to appropriate polypeptides.

The examples which follow serve to illustrate the present invention but without intending to restrict it to them.

Of these, Examples 3 and 4 are intended to demonstrate that the fusion protein cleavages obtained in Examples 1 and 2 are attributable to the incorporation of a polyglycine sequence and not to a degradation of $(X_1 \ldots X_n)$ or $(Y_1 \ldots Y_m)$.

EXAMPLE 1

Cleavage of a polyglycine-containing fusion protein

A construction in which a segment of β-galactosidase is linked via a $(Gly)_{18}$-peptide and a synthetic hexapeptide to proinsulin is used. Proinsulin forms the carboxyl end of the fusion protein. The protein is enriched to the extent of about 40%.

This protein is dissolved at a concentration of 20 mg/ml in buffer (8 M urea; 50 mM Tris/HCl; pH 7.5) and adjusted, by slow dilution with 50 mM Tris/HCl, pH 7.5 and 8 M urea, pH 7.5, to various urea concentrations (see Table 1) and a protein concentration of 2 mg/ml or 10 mg/ml. Lysostaphin ((®)SIGMA) is added in the enzyme/substrate ratio of 1:100 or 1:1000 to the solutions, which are slightly cloudy in each case and are maintained at 37° C. Samples are taken at defined times and analyzed by SDS electrophoresis. The selective degradation of the fusion protein at the polyglycine sequence is evident from the decrease in the fusion protein band and the formation of a new band for the galactosidase fragment having a molecular weight lower by about 10,000 Dalton.

TABLE 1

| Protein concentration (mg/ml) | Enzyme/substrate ratio | Urea concentration (M) | Reaction (>95% decrease in the fusion protein band) (Hours) |
|---|---|---|---|
| 2 | 1:100 | 4 | >20 |
| 2 | 1:100 | 3 | 20 |
| 2 | 1:100 | 2 | 5 |
| 2 | 1:100 | 1 | 2 |
| 10 | 1:100 | 2 | 20 |

Table 1 lists the times after which the area, evaluated by densitometry of the SDS electrophoresis, for the original fusion band has fallen below 5%. The values obtained are between 1 and 20 hours depending on the urea concentration and enzyme/substrate ratio. The presence of a reducing agent, for example dithioerythritol (DTE, Cleland's reagent), which is advantageous for dissolving the fusion protein, has no significant effect on the activity of the enzyme.

EXAMPLE 2

Cleavage of a fusion protein in suspension

The same construction as in Example 1 is used, but not in isolated, dried form. On the contrary, a suspension as is customarily produced when obtaining the inclusion bodies, and which contains about 50 g/l fusion protein, at about 200 g/l dry matter (90% protein), is used. 10 ml of this suspension are diluted to 200 ml with 50 mM Tris/HCl, pH 7.5, and 20 mg of lysostaphin ((®)SIGMA) are added. After 20 hours at 37° C., SDS gel electrophoresis shows only small remaining traces of unfragmented fusion protein.

EXAMPLE 3

Incubation of proinsulin with lysostaphin

Proinsulin (human) is dissolved at a concentration of 1 mg/ml in 50 mM Tris/HCl, pH 7.5, and lysostaphin is added in the enzyme/substrate ratio 1:100. The solution is maintained at 37° C. Samples are taken after 1, 3, 5 and 20 hours and analyzed by reversed phase HPLC. This reveals no evidence of degradation of the proinsulin by lysostaphin.

EXAMPLE 4

Attempt at cleavage of a fusion protein without a polyglycine sequence

A construction in which a segment of β-galactosidase is linked via a synthetic hexapeptide to proinsulin is used. Proinsulin forms the carboxyl end of the fusion protein. The fusion protein is enriched to the extent of about 80%. This protein is dissolved at a concentration of 20 mg/ml in buffer (8 M urea; 50 mM Tris/HCl; pH 7.5) and adjusted to a protein concentration of 2 mg/ml by slow dilution with 50 mM Tris/HCl, pH 7.5. lysostaphin ((®)SIGMA) in the enzyme/substrate ratio 1:100 is added to the slightly cloudy solution, which is maintained at 37° C. Analysis of samples by SDS electrophoresis shows no degradation of the fusion protein even after 20 hours.

We claim:

1. A method for the preparation of proinsulin by enzymatic cleavage of a fusion protein, wherein
   (a) a fusion protein is formed by linking proinsulin to a peptide as follows:

$$(Y_1 \ldots Y_m) - (Gly)_{p+q} - (X)$$

where $(Y_1 \ldots Y_m) - (Gly)_p$ represents the sequence which is to be eliminated and $(Gly)_q - (X)$ represents proinsulin;

X and Y denote, independently of one another, natural amino acids;

m is greater than 1;

p is greater than 0;

p+q is between 2 and 100, and if $Y_m$ is Gly, p+q can be less than 2, and p can be 0; and (b) cleaving the fusion protein with lysostaphin.

2. The method as claimed in claim 1, wherein p+q is between 2 and 30.

3. The method as claimed in claim 2, wherein p+q is between 2 and 18.

4. The method as claimed in claim 1, wherein betagalactosidase is employed as the sequence to be eliminated.

5. The method as claimed in claim 4, wherein a segment of beta-galactosidase is linked to proinsulin by a $(Gly)_{18}$ peptide.

* * * * *